(12) United States Patent
Davidson et al.

(10) Patent No.: US 8,962,003 B2
(45) Date of Patent: Feb. 24, 2015

(54) INSECT BEHAVIOUR MODIFYING COMPOUNDS

(75) Inventors: Melanie Millicent Davidson, Christchurch (NZ); David Austin John Teulon, Christchurch (NZ); Nigel Brian Perry, Dunedin (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 2572 days.

(21) Appl. No.: 10/579,245

(22) PCT Filed: Nov. 12, 2004

(86) PCT No.: PCT/NZ2004/000285
§ 371 (c)(1),
(2), (4) Date: Jan. 31, 2008

(87) PCT Pub. No.: WO2005/046330
PCT Pub. Date: May 26, 2005

(65) Prior Publication Data
US 2008/0241205 A1    Oct. 2, 2008

(30) Foreign Application Priority Data
Nov. 13, 2003 (NZ) ........................ 529495

(51) Int. Cl.
*A01N 43/40* (2006.01)
*A01P 7/04* (2006.01)

(52) U.S. Cl.
CPC ..................................... *A01N 43/40* (2013.01)
USPC ............................ 424/405; 514/336; 514/354

(58) Field of Classification Search
None
See application file for complete search history.

(56) References Cited

U.S. PATENT DOCUMENTS

| 4,212,664 | A | * | 7/1980 | Takeuchi et al. | ............... 504/260 |
| 4,889,870 | A | | 12/1989 | Wegner et al. | ................. 514/429 |
| 5,922,880 | A | | 7/1999 | Sakamoto et al. | ............ 546/296 |

FOREIGN PATENT DOCUMENTS

| GB | 347451 | 4/1931 |
| WO | 96/11909 | 4/1996 |
| WO | WO02/068442 | 9/2002 |
| WO | WO03/055309 | 7/2003 |

OTHER PUBLICATIONS

Office Action issued Jul. 27, 2010 from Japan Patent Office in corresponding Japanese patent application No. 2006-539420 (English translation provided).
Abstract of JP-A-09-151172, published Jun. 10, 1997, applicant: N. Sakamoto et al.
Abstract of JP-A-64-038003, published Feb. 8, 1989, applicant: M. Hideaki et al.
Abstract of JP-A-02-049703, published Feb. 20, 1990, applicant: S. Takeshi et al.
Abstract of JP-A-01-261303, published Oct. 18, 1989, applicant: M. Hideaki et al.
K. MacDonald et al., "Effects of Alarm pheromone on landing and take-off by adult western flower thrips," Entomologia Experimentalis et Applicata, 2002, vol. 103, No. 3, p. 279-281.
E. Koscher et al., "Assessing the attractiveness of volatile plant compounds to western flower thrips *Frankliniella occidentalis*," Journal of Chemical Ecology, 2000, vol. 26, No. 12, pp. 2643-2655.
Pankiewicz-Nowicka et al, Annals of the Entological Soc, 1986, pp. 293-299, Attraction by Selected Organic Compounds to . . . .
Penman et al, Jour of Chem Ecology, vol. 8, No. 10, 1982, pp. 1299-1303, Ethyl Nicotinate: A Chemical Attractant for Thrips . . . .
Teulon et al, Jour of Economical Entomology 86(5), 1993, pp. 1405-1415, Volatile Chemicals for Thrips (Thysanoptera: . . . .
Hamilton et al, Jour of Chem Ecology, vol. 31, No. 6, Jun. 2005, pp. 1369-1379, Identification of a Male-Produced Aggregation . . . .
MacDonald et al, Jour of Chem Ecology, vol. 29, No. 10, Oct. 2003, pp. 2385-2389, Analysis of Anal Droplets of the Western . . . .

* cited by examiner

*Primary Examiner* — Kortney L Klinkel
(74) *Attorney, Agent, or Firm* — Jacobson Holman, PLLC.

(57) ABSTRACT

The invention provides methods for controlling thrips populations using thrips-repelling and/or thrips-attracting agents. The invention also provides methods of preventing or minimizing damage to plants by use of the same.

14 Claims, No Drawings

INSECT BEHAVIOUR MODIFYING COMPOUNDS

This is a nationalization of PCT/NZ04/000285 filed Nov. 12, 2004 and published in English.

TECHNICAL FIELD

The present invention relates to a method for controlling, surveying or regulating thrips populations, including populations of *Thrips obscuratus, Thrips tabaci* and *Frankliniella occidentalis*. The invention particularly relates to a method of preventing thrips-induced damage to plants.

BACKGROUND

Insect pests are a worldwide problem, often causing damage to cultivated crops and plants. Thrips, comprising the order Thysanoptera, are one common insect pest. By feeding on flowers and leaves, and laying their eggs within the plant, thrips can cause serious damage to crops. Some thrips also spread plant damaging viruses.

A thrips infestation can be hard to detect, especially at low densities, as the insects are often active within the enclosed parts of a plant such as the buds. This also makes them difficult to reach with pesticides. In addition, environmental concerns mean that it is becoming less desirable to use pesticides to control insect populations, and many species of thrips are becoming resistant to pesticides. Thus, there is an ongoing need for methods that monitor thrips at low densities, and alternative methods of controlling thrips, in order to lessen the potential for damage to cultivated crops and plants.

It has been proposed that scent may be used by thrips for detection of and orientation to their hosts. Thus, certain aromatic compounds can act as attractants and/or arrestants for thrips. It is therefore possible to lure the insects using suitable traps baited with attractant compounds.

Repellant compounds may also protect crop plants, particularly if used with separate traps baited with attractant compounds.

Ethyl nicotinate is a potent attractant for *Thrips obscuratus* (D. R. Penman, G. O. Osborne, S. P. Worner, R. B. Chapman and G. F. McLaren, *Journal of Chemical Ecology*, (1982) 8, 1299). These thrips are attracted to ripe peaches, but ethyl nicotinate is even more attractive to the insects than ripe fruit. Ethyl nicotinate is less attractive to *Frankliniella occidentalis* and varied in its attractiveness to *Thrips tabaci* (Teulon, D. A. J., Penman, D. R. and Ramakers, P. M. J. (1993) *J. Econ. Entomol.*, 86, 1405-1415).

A number of other aromatic compounds have been reported as attractants for various thrips species. For example, anisaldehyde, in combination with blue sticky traps (H. F. Brødsgaard, *WPRS Bull.* (1990) XIII, 36) or yellow water traps (Teulon, D. A. J., Hollister, B. and Cameron, E. A. (1993) *IBOC/WPRS Bull.*, 16, 177-180), is an attractant for *Frankliniella occidentalis*. Anisaldehyde varies in its attractiveness to *Thrips tabaci* (Teulon, D. A. J., Penman, D. R. and Ramakers, P. M. J. (1993) *J. Econ. Entomol.*, 86, 1405-1415) and is an attractant for *Thrips hawaiiensis* but not for *Thrips coloratus* (T. Murai, T. Imai and M. Maekawa, *Journal of Chemical Ecology*, (2000) 26, 2557).

In field trials, methyl anthranilate has been shown to be an attractant for *Thrips hawaiiensis* and *Thrips coloratus*, but not for *Thrips tabaci* (T. Mural, T. Imai and M. Maekawa, *Journal of Chemical Ecology*, (2000) 26, 2557). Furthermore, ethyl anthranilate is an attractant for *Thrips hawaiiensis, Thrips coloratus*, and *Thrips flavus* (T. Imai, M. Maekawa and T. Mural, *Appl. Entomol. Zool.* (2001) 36, 475).

Decyl acetate and dodecyl acetate have been reported as alarm pheromones of *Frankliniella occidentalis* with repellant activity (K. M. MacDonald, J. G. C. Hamilton, R. Jacobson and W. D. J. Kirk, *Entomologia Experimentalis et Applicata* (2002), 103, 279). These compounds have been combined with insecticides to control field infestations of *Frankliniella occidentalis* (D. F. Cook, I. R. Dadour and W. J. Bailey, *Int. J. Pest Management* (2002), 48, 287).

JP Patent 48006537 describes an apparatus containing the attractants anisaldehyde and(or) cinnamaldehyde used to trap and kill insects such as thrips.

JP Patents 02049703, 01261303 and 01038003 describe respectively eugenol and/or beta-ionone, cinnamic aldehyde and/or o-methoxycinnamic aldehyde, or thiazole derivatives as repellants for thrips, especially against *Thrips palmi*.

WO 03/055309 describes a method of surveying or controlling thrips using behaviour modifying compounds. Monoterpene esters were shown to be attractive to *Frankliniella occidentalis* by testing in a Y-tube olfactometer, rather than in field trials.

It is an object of this invention to provide a method for controlling, surveying or regulating thrips or to at least provide the public with a useful choice.

STATEMENTS OF INVENTION

In a first aspect, the invention provides a method of controlling, surveying or regulating thrips populations comprising providing at least one thrips behaviour-modifying compound of formula (I)

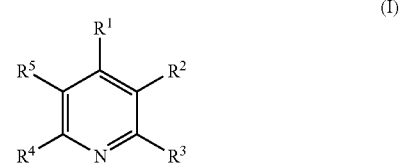

wherein:

$R^1$ is selected from

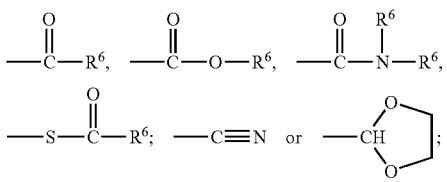

$R^2$, $R^3$, $R^4$ and $R^5$ are each independently selected from hydrogen, halogen, hydroxyl, nitro, or optionally substituted straight or branched chain alkyl, alkenyl, or alkynyl; and $R^6$ is selected from hydrogen or optionally substituted straight or branched chain alkyl, cycloalkyl, alkenyl or alkynyl.

It is preferred that $R^2$, $R^3$, and $R^5$ are all hydrogen and $R^4$ is halogen.

Alternatively, it is preferred that $R^2$, $R^3$, $R^4$ and $R^5$ are all hydrogen.

It is further preferred that $R^1$ is

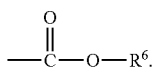

Alternatively, it is preferred that $R^1$ is

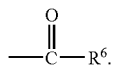

Alternatively, it is preferred that $R^1$ is

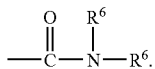

When $R^1$ is

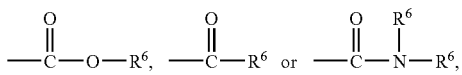

it is preferred that $R^6$ is straight or branched chain alkyl.

In a preferred embodiment, the at least one thrips behaviour-modifying compound of formula (I) is as defined above provided that when $R^1$ is

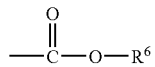

and $R^2$, $R^3$, $R^4$ and $R^5$ are all hydrogen, $R^6$ is not isopentenyl or hexyl.

Preferred compounds of formula (I) include:
methyl isonicotinate;
ethyl isonicotinate;
propyl isonicotinate;
isopropyl isonicotinate;
decyl isonicotinate;
ethyl 2-chloro-isonicotinate;
pyridine, 4-(1,3-dioxolan-2-yl);
di-isopropyl isonicotinamide;
4-formyl pyridine;
methyl 4-pyridyl ketone;
ethyl 4-pyridyl ketone;
propyl 4-pyridyl ketone;
4-cyanopyridine; and
4-pyridyl thioacetate.

The invention preferably provides a method of controlling, surveying or regulating thrips populations comprising providing at least one thrips behaviour-modifying compound of formula (I) in a holding device, where the compound of formula (I) attracts thrips to the holding device. The holding device preferably includes a means for catching, immobilising or killing thrips. Suitable holding devices include water traps, sticky traps or pheromone traps.

In a second aspect, the invention provides a method of preventing or minimising damage to plants caused by thrips comprising attracting thrips away from the plants by providing at least one thrips-attracting compound of formula (I) as defined above.

It is preferred that $R^2$, $R^3$, and $R^5$ are all hydrogen and $R^4$ is halogen.

Alternatively, it is preferred that $R^2$, $R^3$, $R^4$ and $R^5$ are all hydrogen.

It is further preferred that $R^1$ is

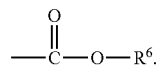

When $R^1$ is

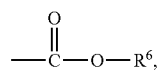

it is preferred that $R^6$ is straight or branched chain alkyl.

Alternatively, it is preferred that $R^1$ is

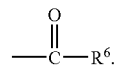

When $R^1$ is

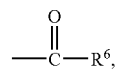

it is preferred that $R^6$ is straight or branched chain alkyl.

Alternatively, it is preferred that $R^1$ is

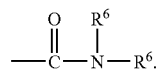

When $R^1$ is

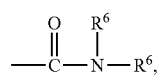

it is preferred that $R^6$ is straight or branched chain alkyl.

In a preferred embodiment, the at least one thrips-attracting compound of formula (I) is as defined above provided that when $R^1$ is

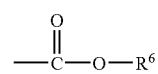

and $R^2$, $R^3$, $R^4$ and $R^5$ are all hydrogen, $R^6$ is not isopentenyl or hexyl.

Preferred compounds of formula (I) include:
methyl isonicotinate;
ethyl isonicotinate;
propyl isonicotinate;
isopropyl isonicotinate;
decyl isonicotinate;
ethyl 2-chloro-isonicotinate;
pyridine, 4-(1,3-dioxolan-2-yl);
di-isopropyl isonicotinamide;
4-formyl pyridine;
methyl 4-pyridyl ketone;
ethyl 4-pyridyl ketone; and
propyl 4-pyridyl ketone.

In a third aspect, the invention provides a method of preventing or minimising damage to plants caused by thrips, comprising repelling thrips away from the plants by providing at least one thrips-repelling compound of formula (I) as defined above.

It is preferred that $R^1$ is CN.

Alternatively, it is preferred that $R^1$ is

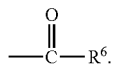

Alternatively, it is preferred that $R^1$ is

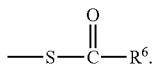

When $R^1$ is

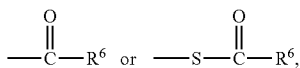

it is preferred that $R^6$ is straight or branched chain alkyl.

In a preferred embodiment, the at least one thrips-repelling compound of formula (I) is as defined above provided that when $R^1$ is

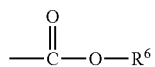

and $R^2$, $R^3$, $R^4$ and $R^5$ are all hydrogen, $R^6$ is not isopentenyl or hexyl.

Preferred compounds of formula (I) include:
4-formyl pyridine;
4-cyanopyridine; and
4-pyridyl thioacetate.

In a fourth aspect, the invention provides a method of controlling, surveying or regulating thrips populations comprising providing at least one-thrips-attracting compound of formula (I) as defined above and at least one thrips-repelling compound of formula (I) as defined above.

In a preferred embodiment, the at least one thrips-attracting compound of formula (I) and the at least one thrips-repelling compound of formula (I) are as defined above provided that when $R^1$ is

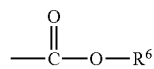

and $R^2$, $R^3$, $R^4$ and $R^5$ are all hydrogen, $R^6$ is not isopentenyl or hexyl.

Preferably, the thrips-attracting compound is selected from the group comprising;
  methyl isonicotinate, ethyl isonicotinate, propyl isonicotinate, isopropyl isonicotinate, decyl isonicotinate, ethyl 2-chloro-isonicotinate, pyridine, 4-(1,3-dioxolan-2-yl), di-isopropyl isonicotinamide, 4-formyl pyridine, methyl 4-pyridyl ketone, ethyl 4-pyridyl ketone and propyl 4-pyridyl ketone;
and the thrips-repelling compound is selected from the group comprising;
  4-formyl pyridine; 4-cyanopyridine and 4-pyridyl thioacetate.

In a fifth aspect, the invention provides a method of controlling, surveying or regulating thrips populations comprising providing at least one thrips behaviour-modifying compound of formula (I) as defined above and at least one other thrips attractant or thrips repellant.

Preferably, the at least one other thrips attractant or thrips repellant is selected from the group comprising:
  ethyl nicotinate, anisaldehyde, cinnamaldehyde, methyl anthranilate, ethyl anthranilate, decyl acetate, dodecyl acetate, eugenol, beta-ionone, o-methoxy cinnamic aldehyde, methyl salicylate, ethyl salicylate, monoterpene 1,8-cineole, salicaldehyde, o-aminoacetophenone, isobornyl valerate, methyl benzoate, ethyl benzoate, 2-phenyl ethanol and p-allyl anisole.

In a sixth aspect, the invention provides a holding device for catching, immobilising or killing thrips, which device contains a thrips-attracting compound of formula (I) as defined above.

Plants that can be protected include onions, lettuce, cabbages and other crucifers, greenhouse vegetables and fruits, flower crops, or any other economically important plants that suffer from thrips infestations.

The methods of the invention may be practised for any species of thrips. Preferably, the methods of the invention may be practiced on species of thrips belonging to the suborder Terebrantia, in particular *Thrips tabaci* and *Frankliniella occidentalis*.

DETAILED DESCRIPTION

The term "alkyl", as used herein, means a straight or branched chain saturated monovalent hydrocarbon radical, preferably a $C_1$-$C_{20}$ alkyl group, more preferably a $C_1$-$C_{10}$ alkyl group, most preferably a $C_1$-$C_5$ alkyl group, including but not limited to methyl, ethyl, n-propy, iso-propyl, n-butyl, iso-butyl, sec-butyl, tert-butyl, n-pentyl, iso-pentyl, neo-pentyl, tert-pentyl and the like.

The term "alkenyl", as used herein, means a straight or branched chain hydrocarbon radical having at least one double bond, preferably a $C_1$-$C_{20}$ alkenyl group, more preferably a $C_1$-$C_{10}$ alkenyl group; most preferably a $C_1$-$C_5$ alkenyl group, including but not limited to ethenyl, propenyl, 1-butenyl, 2-butenyl, pentenyl and the like.

The term "alkynyl", as used herein, means a straight or branched chain hydrocarbon radical having at least one triple bond, preferably a $C_1$-$C_{20}$ alkynyl group, more preferably a $C_1$-$C_{10}$ alkynyl group, most preferably a $C_1$-$C_5$ alkynyl group, including but not limited to ethynyl, propynyl, 1-butynyl, 2-butynyl, pentynyl and the like.

The term "halo", as used herein, refers to F, C, Br or I, preferably F or Cl.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "optionally substituted", as used herein, means that a substituent may be covalently attached to, appended to, or if appropriate, fused to, the parent group. A wide variety of substituents are well known, and methods for their formation and introduction into a variety of parent groups are also well known. Examples of substituents include, but are not limited to, the following:

halo, hydroxy, alkyl, ether, alkoxy, oxo, imino, formyl; carboxy, carboxylate, acyloxy, amido (carbamoyl, carbamyl, aminocarbonyl), acylamido (acylamino), amino, cyano (nitrile, carbonitrile), nitro, sulfhydryl (thiol, mercapto), sulfonamino, sulfinamino, sulfamyl; and sulfonamido. Alkyl is generally preferred as a substituent group.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

The term "thrips" as used herein, refers to any one of numerous small species of the order Thysanoptera, especially those belonging to the sub-order Terebrantia, including, but not limited to *Thrips obscuratus, Thrips tabaci* and *Frankliniella occidentalis*. The methods of this invention may be used to control a variety of different species of thrips, including *Thrips obscuratus, Thrips tabaci* and *Frankliniella occidentalis*.

The term "thrips behaviour-modifying compound" as used herein, refers to a compound that influences the behaviour of thrips by attracting the thrips to the source of the compound or repelling the thrips from the source of the compound.

The term "thrips-attracting compound" as used herein is intended to encompass thrips behaviour-modifying compounds with attractant and/or arrestant modes of action. An arrestant does not attract per se, but retains an organism once in the vicinity. An arrestant may slow the linear progression of the organism by reducing the actual speed of locomotion, or by increasing the turning rate.

The term "thrips-repelling compound" as used herein is intended to encompass thrips behaviour-modifying compounds with repellant activity. A thrips-repelling compound will cause the thrips to spend less time in a given target area (an area to which the thrips-repelling compound has been applied), than in an available non-target area. The thrips may be deterred from entering the target area, or from remaining in the target area.

The applicant has now discovered a new class of thrips behaviour-modifying agents that can be used in horticultural and agricultural applications. Such behaviour-modifying agents include compounds that are attractive and/or repellant to thrips and cause them to modify their behaviour accordingly.

In its broadest aspect, the present invention provides a method of controlling, surveying or regulating thrips populations using a behaviour-modifying compound of formula (I)

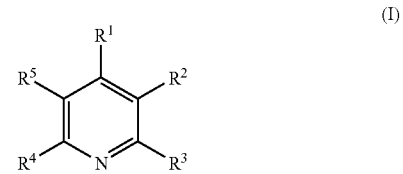

(I)

wherein:
R$^1$ is selected from

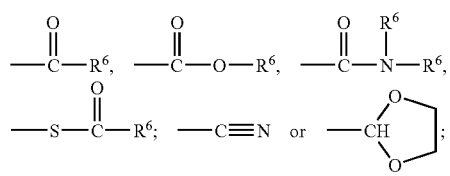

R$^2$, R$^3$, R$^4$ and R$^5$ are each independently selected from hydrogen, halogen, hydroxyl, nitro, or optionally substituted straight or branched chain alkyl, alkenyl, or alkynyl; and R$^6$ is selected from hydrogen or optionally substituted straight or branched chain alkyl, cycloalkyl, alkenyl or alkynyl.

Preferred compounds for use in the methods of the invention are compounds of formula (I) wherein one or more of R$^2$, R$^3$, R$^4$ and R$^5$ is halogen, in particular R$^2$ or R$^3$. Especially preferred is ethyl 2-chloroisonicotinate which was found to be a strong attractant of *Frankliniella occidentalis*. Without being bound by theory it is postulated that electronegative atoms such as halogens affect the electron density on the pyridine ring and at the carbonyl group so as to increase binding at the relevant receptor site in the insect.

Other preferred compounds of formula (I) for use in the methods of the invention include alkyl isonicotinate esters which result when R$^1$ is

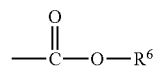

and R$^6$ is straight or branched chain alkyl. Alkyl isonicotinate esters have been found to be strongly attractive to *Thrips tabaci*. This is an unexpected finding as structurally similar compounds such as ethyl nicotinate are not known as strong attractants for *Thrips tabaci*. The results of tests using methyl isonicotinate, ethyl isonicotinate, isopropyl isonicotinate, propyl isonicotinate and decyl isonicotinate are shown in Table 1.

The thrips behaviour-modifying activity of a compound of formula (I) may vary with respect to the particular species of thrips against which it is being tested. For example, hexyl isonicotinate was not found to be significantly attractive to *Thrips obscuratus* or *Thrips tabaci* and the alkenyl isonicotinate ester, isopentenyl isonicotinate was not found to be significantly attractive or repulsive to *Frankliniella occidentalis*.

However, these compounds may still be useful in the methods of the invention as thrips behaviour-modifying compounds for other untested species. Additionally, it is possible that they have thrips behaviour-modifying properties when used in different amounts, under different conditions, and/or in combination with other thrips behaviour-modifying agents.

In addition to alkyl isonicotinate esters, the structurally similar alkyl 4-pyridyl ketone compounds (where $R^1$ is

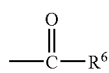

and $R^6$ is straight or branched chain alkyl) are also preferred for use in the methods of the invention.

Methyl 4-pyridyl ketone and ethyl 4-pyridyl ketone have been found to be attractants for *Thrips tabaci* (Table 1) and propyl 4-pyridyl ketone has been found to be an attractant for *Frankliniella occidentalis* (Table 2).

Alkyl isonicotinamides are also preferred compounds of formula (I) for use in the methods of the invention. Di-isopropyl isonicotinamide was found to be an attractant for *Frankliniella occidentalis* (Table 2).

Other compounds of formula (I) such as 4-cyanopyridine and 4-pyridyl thioacetate show thrips-repellant activity. It is possible for a compound to be both a thrips-attractant and a thrips-repellant depending on the concentration to which the thrips is exposed. For example, 4-formyl pyridine was found to be an attractant for *Frankliniella occidentalis* at low concentration and a repellant at high concentration (Table 2).

Preferred compounds of formula (I) include:
methyl isonicotinate;
ethyl isonicotinate;
propyl isonicotinate;
isopropyl isonicotinate;
decyl isonicotinate;
ethyl 2-chloro-isonicotinate;
pyridine, 4-(1,3-dioxolan-2-yl);
di-isopropyl isonicotinamide;
4-formyl pyridine;
methyl 4-pyridyl ketone;
ethyl 4-pyridyl ketone;
propyl 4-pyridyl ketone;
4-cyanopyridine; and
4-pyridyl thioacetate.

In its broadest aspect, the present invention provides a method of controlling, surveying or regulating thrips populations using a thrips behaviour-modifying compound of formula (I) as defined above.

A compound of formula (I) is efficacious as a thrips behaviour-modifying compound if it is able to demonstrate behaviour-modifying properties such as attracting (including arresting) or repelling thrips, including *Thrips tabaci* and *Frankliniella occidentalis*. Thrips behaviour-modifying compounds include thrips-attracting and thrips-repelling compounds.

The thrips behaviour-modifying activity of a compound may be evaluated in a glass Y-tube olfactometer following the method described by de Kogel et al. (de Kogel, W. J., Koschier, E. H. and Visser, J. H. *Proc. Exper. & Appl. Entomol., N. E. V. Amsterdam*, (1999) 10, 131-135.) and Koschier et al. (Koschier, E. H., De Kogel, W. J. and Visser, J. H. (2000) *Jounrnal of Chemical Ecology*, 26, 2643-2655).

Activity may also be assessed in field trials utilising holding devices containing the potential thrips behaviour-modifying compound.

The invention also provides methods of preventing or minimising damage to plants caused by thrips.

In one embodiment the method comprises attracting thrips away from the plants by providing at least one thrips-attracting compound of formula (I) as defined above.

In another embodiment the method comprises repelling thrips from the plants by providing at least one thrips repelling compound of formula (I) as defined above.

In the above methods, the thrips behaviour-modifying compound can be provided by any means known in the art. For example, the compounds may be provided in dispensers that allow emission of the compounds. Examples of such dispensers include but are not limited to pads, beads, rods, spirals or balls composed of rubber, plastic, leather, cotton, wood or wood products that are impregnated with the behaviour-modifying compound.

The behaviour-modifying compound may also be applied directly to surfaces in the vicinity of a population of thrips. The location to which the behaviour-modifying compound is to be provided depends on whether it is a thrips-attractant or thrips-repellant.

For example, a thrips-attracting compound may be placed in a "holding device". Such a holding device is preferably designed to release an effective amount of the thrips-attracting compound. The device is positioned in an area infested (or potentially infested) with thrips. The aroma of the compound attracts thrips to the holding device. The insects may then be caught and immobilised or killed within the holding device, for example, by including within the device, a pesticide which is toxic to thrips. Contact pesticides are particularly preferred.

The invention also provides a holding device for catching, immobilising or killing thrips wherein the device contains at least one thrips behaviour-modifying compound of formula (I) as defined above.

It will be appreciated by a person skilled in the art that a variety of different holding devices are possible. Suitable examples of such devices include water traps, sticky traps, and pheromone traps. Holding devices may also be coloured to provide additional attraction for thrips. Further examples of devices designed for capturing thrips are described in Lewis T. 1997, Thrips as Crop Pests, CAB International, Oxon.

Thrips populations can be surveyed by counting the number of insects caught. Based on the estimated population, decisions can be made regarding the need for population control. For example, a discovery of a high population of thrips may necessitate the use of methods for removal of the thrips, such as provided by the methods of the invention. Conversely, a discovery of a low thrips population may lead to a decision that it is sufficient to continue monitoring the population.

Alternatively, thrips may be attracted to an area where they are exposed to a disease, which they may then spread to other thrips; or to predators and/or parasitoids released to control them.

The invention also provides a method of controlling, surveying or regulating thrips comprising providing at least one thrips-attracting compound of formula (I) as defined in claim 1 and at least one thrips-repelling compound of formula (I) as defined in claim 1.

By providing both thrips-attractant and thrips-repellant concurrently, the above "push-pull" method is especially effective in modifying the behaviour of the thrips. A thrips-attracting compound and a thrips-repelling compound can be provided as described above.

The invention also provides a method of controlling, surveying or regulating thrips populations comprising providing at least one behaviour-modifying compound of formula (I) as defined above and at least one other thrips-attractant or thrips-repellant.

Other thrips-attractants/repellants that can be used in the method of the invention include but are not limited to ethyl nicotinate, anisaldehyde, cinnamaldehyde, methyl anthranilate, ethyl anthranilate, decyl acetate, dodecyl acetate, eugenol, beta-ionone, o-methoxy cinnamic aldehyde, methyl salicylate, ethyl salicylate, monoterpene 1,8-cineole, salicaldehyde, o-aminoacetophenone, isobornyl valerate, methyl benzoate, ethyl benzoate, 2-phenyl ethanol and p-allyl anisole.

The at least one thrips-attracting compound of formula (I) can be used in conjunction with one or more other thrips-attractants to attract thrips away from the plants. Conversely, at least one thrips-repelling compound of formula (I) can be used in conjunction with one or more other thrips-repellants to repel thrips away from the plants.

Alternatively, at least one thrips-attracting compound of formula (I) can be used in conjunction with one or more other thrips-repellants in a "push-pull" method to attract thrips away from the plants, or otherwise survey or regulate thrips populations. Similarly, at least one thrips-repelling compound of formula (I) can be used in conjunction with one or more other thrips-repellants to repel thrips away from the plants, or otherwise survey or regulate thrips populations.

The thrips behaviour-modifying compounds of formula (I) may be provided in pure form or in solution. Suitable solvents are organic solvents such as the lower alkanols such as ethanol; alkanes such as hexane, kerosene and similar petroleum oils, ethers, ketones, aldehydes and the like.

The concentration of behaviour-modifying compound used in the methods of the invention is not critical. The lower limit is defined by that amount required to form an effective dose. In some situations the pure compound will be used. Useful amounts to produce thrips-behaviour modification will depend on the particular application technique used, the efficacy of the particular behaviour-modifying compound, the conditions at the time of application, and the size and nature of the area to be targeted. Such amounts can readily be determined by those skilled in the art. For example, by employing the methodologies described in the Examples below.

Field trial results for selected compounds are summarised in Table 1, Y-tube olfactometer results in Table 2, and greenhouse trials results are summarised in Table 3.

It will also be appreciated that the methods of the present invention may be employed to control or survey thrips in a variety of different locations. For example, the method may be practised in an outdoor location or in an enclosed structure such as a greenhouse. These methods may be used to control or survey thrips infestations (or possible infestations) of crops such as onions, lettuces, cabbages and other crucifers, greenhouse vegetables and fruits, flowers, or any other economically important plants that suffer from thrips infestations.

It will be clear to a person skilled in the art that the methods of this invention may be used for early detection of a possible thrips infestation, or for controlling thrips during an actual infestation.

EXAMPLES

The invention will now be described in further detail with reference to the following examples. It is to be appreciated that the invention is not limited to these examples.

Selected compounds of the invention were tested for their thrips behaviour modifying properties. Compounds were either purchased from commercial sources or synthesised. Synthetic procedures are outlined in Example 1, field trial procedures are outlined in Example 2, Y-tube olfactometer bioassays in Example 3, and greenhouse trials in Example 4. Table 1 shows the structural formulae of the compounds tested, together with their attractant activities towards *Thrips tabaci* and *Thrips obscuratus*. Table 2 shows attractant and repellant activities towards *Frankliniella occidentalis*. Table 3 shows attractant activities towards *Frankliniella occidentalis*.

Example 1

Syntheses

Isopropyl sonicotinate.

A suspension of isonicotinic acid (Aldrich, 5 g) in oxalyl chloride (10.4 ml) was refluxed for 24 hours. Excess oxalyl chloride was removed by evaporation in vacuo to leave the acid chloride. Addition of isopropanol (20 ml, drop wise), standing at room temperature for 2 hours, then evaporation in vacuo gave the crude isopropyl nicotinate. Aqueous sodium bicarbonate solution (100 ml) was added, then the product extracted into dichloromethane (2×100 ml). This was dried, then evaporated in vacuo to give isopropyl isonicotinate [Registry No. 125294-42-0] as a creamy white, oily looking solid (5.60 g, 83%): UV (methanol) $\lambda_{max}$ (log $\epsilon$) 212 (3.95), 274 (3.43) nm.

Propyl Isonicotinate.

Isonicotinic acid (Aldrich, 10 g) was refluxed with excess thionyl chloride (50 ml) for one hour. Excess thionyl chloride was removed by evaporation in vacuo to leave the acid chloride. Propanol (12.5 ml) was added and stirred for 30 minutes. Aqueous sodium bicarbonate solution (100 ml) was added, then the product extracted into dichloromethane (2×200 ml). This was dried then evaporated in vacuo to give propyl isonicotinate [Registry No. 90610-01-8] as a transparent straw coloured gum (5.10 g, 38%). $^1$H NMR (CDCl$_3$) 8.76 (2H, m), 7.84 (2H, m), 4.31 (2H, t, J 7 Hz), 1.80 (2H, sextet, J 7 Hz), 1.02 (3H, t, J 7 Hz); UV (methanol) $\lambda_{max}$ (log $\epsilon$) 212 (3.86), 274 (3.33) nm.

n-Propyl 4-pyridyl Ketone.

Pyridinium chlorochromate (4.27 g, 19.84 mmol) was suspended in dry dichloromethane (50 ml) in a round-bottom flask under an atmosphere of N$_2$. After stirring for 5 min, 1-(4-pyridyl)-1-butanol (2.0 g, 13.23 mmol) in dry dichloromethane (10 ml) was added. The reaction was followed by t.l.c. and once complete (~2 h) anhydrous ether (70 ml) was added. The supernatant was decanted and the residual black gum was washed with anhydrous ether (4×100 ml). The combined organic fractions were concentrated in vacuo, and the black tar-like substance was purified by flash chromatography [EtOAc as eluant] to give a brown oil. The product was then purified by silica gel column chromatography [3:1 EtOAc:hexanes as eluant] to give n-propyl 4-pyridyl ketone [Registry No. 1701-71-9] as a yellowy-green oil (520 mg, 27%). $^1$H NMR (300 MHz, CDC$_3$): δ 1.01 (3H, t, J=7.5 Hz, CH$_3$), 1.78 (2H, sxt, J=7.4 Hz, —CH$_2$—), 2.95 (2H, t, J=7.2

Hz, CH$_2$—CO), 7.72 (2H, d, J=5 Hz, H-3, H-5), 8.81 (2H, d, J=5 Hz, H-2, H-6) ppm.

4-Pyridyl thioacetate

4-Mercaptopyridine (100 mg, 0.9 mmol) was stirred in ice-cold acetic anhydride (2 ml) overnight. The acetic anhydride was removed in vacuo, and the residue dissolved in EtOAc and washed with sat. NaHCO$_3$. The organic phase was dried (Na$_2$SO$_4$) and solvent removed in vacuo to give the crude 4-pyridyl thioacetate [Registry No. 36875-66-8] as a red oil. $^1$H NMR (300 MHz, CDC$_3$) inter alia: δ 2.48 (3H, s, CH$_3$), 7.37 (2H, d, J=6.0 Hz, H-3, H-5), 8.63 (2H, d; J=6.0 Hz, H-2, H-6) ppm.

Di Isopropyl Isoncotinamide n-Butyl lithium (8.27 ml, 1.6 M in hexanes, 13.23 mmol) was added to diisopropylamine (13.36 mmol, 1.95 ml) in dry THF (10 ml) at −78° C. and stirred for 0.5 h (to make lithium diisopropylamine, LDA). The mixture was warmed to room temp. for 20 min, then cooled down to −78° C. again. Ethyl isonicotinate (1.00 g, 6.62 mmol, 0.91 ml) was dissolved in dry THF (30 mL) and cooled to −78° C. under an atmosphere of argon. The freshly prepared LDA was added to the ethyl isonicotinate solution dropwise. The mixture was left to stir for 1 h, then allowed to warm to room temperature for 0.5 h. The reaction mixture was cooled to −78° C. again and 1,2-dibromotetrafluoroethane (6.62 mmol, 0.79 ml) in THF (10 mL) was added slowly. The reaction was stirred at −78° C. for 1 h, then stirred at room temp. overnight. Water (40 ml) was added. The organic layer was separated, and the aqueous layer was washed with CHCl$_3$ (3×100 ml). The combined organic solutions were dried (Na$_2$SO$_4$) and the solvent removed to give the crude compound. The crude compound was columned [8:2 benzene:acetone as eluant], to give diisopropyl isonicotinamide [Registry No. 77924-05-1]. $^1$H NMR (300 MHz, CDCl$_3$) 8.66 (2H, d, J 6 Hz), 7.19 (2H, d, J 6 Hz), 3.69 (1H, bs), 3.55 (1H, bs), 1.54 (6H, bs) and 1.16 (6H, bs).

Ethyl-2-chloro-Isonicotinate

To a mixture of acetic acid and hydrogen peroxide (30%, 14 ml) was added ethyl isonicotinate (10 g). The solution was heated to 75° C. for 24 h, then reduced to a third of the volume, made basic with aq K$_2$CO$_3$ and extracted into dichloromethane. The CH$_2$Cl$_2$ solution was dried and, evaporated in vacuo to give the N-oxide as a white crystalline solid (10.5 g). The N-oxide (10.5 g) in chloroform (25 ml) was refluxed for 12 h with phosphorus oxychloride (25 ml), cooled, then poured onto ice. The product was extracted into dichloromethane, dried and evaporated to give ethyl-2-chloro-isonicotinate [Registry No. 54453-93-9] as a pale yellow liquid. $^1$H NMR (300 MHz, CDC$_3$) 8.53 (1H, d, J 7 Hz), 7.87 (1H, d, J 2 Hz), 7.76 (1H, dd, J 2, 7 Hz), 4.42 (2H, q, J 8 Hz) and 1.40 (3H, t, J 8 Hz).

4-(1,3-Dioxolan-2-yl)pyridine

A stirred solution of pyridine-4-carboxaldehyde (8.7 ml, 90 mmol), ethylene glycol (10 ml, 180 mmol) and p-toluene sulfonic acid (18.8 g, 99 mmol) in benzene (70 ml) was refluxed overnight. A Dean-Stark apparatus was used to remove water azeotropically from the reaction. After ~15 h the mixture was cooled, then made basic with aq. NaOH (20% w/v, ~30 ml). The benzene layer was isolated and the aqueous layer was washed with dichloromethane until no more product came out (~5×60 ml). The combined organic phases were dried (Na$_2$SO$_4$) and solvent removed in vacuo to give the pure 4-(1,3 dioxolan-2-yl) pyridine [Registry No. 61379-59-7] as a pale yellow liquid that solidified under vacuum (12.57 g, 92%). $^1$H NMR (300 MHz, CDCl$_3$): δ 4.06 (4H, m, O—(CH$_2$)$_2$—O), 5.82 (1H, s, O—CH—O), 7.39 (2H, d, J=6-Hz, H-3, H-5), 8.63 (2H, d, J=6 Hz, H-2, H-6) ppm.

Example 2

Field Trials

Water traps were placed out into a field comprising several species of grasses, white clover (*Trifolium repens* L.) and several weed species (≈100 mm in height). Grass and cereal fields surrounded the field trial area on three sides and poplar (*Poplar nigra* L.) trees on the other, on the Canterbury Agricultural Research Centre campus. Each field trial consisted of five replicates of five treatments including a water control, positive control compound (ethyl nicotinate, ethyl isonicotinate, or benzaldehyde, Table 1) and three test compounds set out in the field in a grid (10×10 m) using a Latin square design with the trial area at least 100 m from the field boundary/shelter belt. White plastic containers (2 L capacity, 16×16× 8.5 cm) containing approximately 1.7 L water, 0.4 ml of formalin (to prevent fungal growth) and 0.08 ml tween were placed above the crop canopy on inverted white (2 L capacity, 16×16×8.5 cm) or black plastic containers (24 cm diameter, 13 cm tall). For each treatment, 1 ml of a compound or water was added to a glass vial (12×32 mm screw thread vial) containing a 4.5 cm$^2$ piece of rolled filter paper (Whatman No. 1) that projected 1 cm above the top of the vial, creating a wick. The glass vial was suspended above the water in the centre of the trap using wire (0.5 mm diameter). The vials were removed after 24 or 48 h and the containers were sealed for transport to a laboratory. The contents from a water trap were poured through a sieve (250 μm mesh) and all insects were washed into a 50 ml Schott bottle within 24 h of collecting them from the field. All thrips were pipetted from each water trap sample and counted. Thrips were mounted on to slides using polyvinyl alcohol glue (1 part polyvinyl alchol: 4 parts water, 1 part lactic acid: 1.25 parts phenyl) from each trap using the following subsample method: less than 50 thrips, all thrips were mounted on to a slide; 50 to 100 thrips, a subsample of 25 thrips were mounted on to a slide; more than 100 thrips, a subsample of 50 thrips were mounted on to a slide. The slides were examined under 100× magnification using a compound microscope to identify thrips species. Subsampled thrips were sexed and identified to species according to Mound and Walker (Mound, L. A. and Walker, A. K. 1982. Terebrantia (Insecta: Thysanoptera). Fauna of New Zealand No. 1.). The mean number of each species for each treatment was calculated by multiplying the proportion of each species within a subsample with the total number of thrips counted in each water trap.

TABLE 1

Attractant activity of selected compounds of the invention, plus a known attractant, towards female *Thrips obseuratus* and *Thrips tabaci* in field trials[1]

| Compound (Registry No.) | Structure | Average ratio of female thrips caught relative to water traps (95% CI[2]) | |
|---|---|---|---|
| | | *Thrips obscuratus* | *Thrips tabaci* |
| Methyl isonicotinate (2459-09-8) | 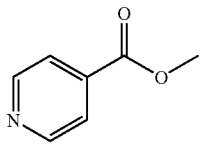 | 44.1* (13.6, 143.6) | 18.9* (9.5, 37.4) |
| Ethyl isonicotinate (1570-45-2) | 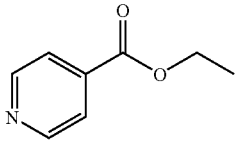 | 31.6* (16.9, 59.1) | 30.8* (19.1, 49.6) |
| Isopropyl isonicotinate (125294-42-0) | 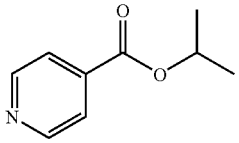 | 9.0* (1.7, 47.5) | 8.8* (4.2, 18.6) |
| n-Propyl isonicotinate (90610-01-8) | 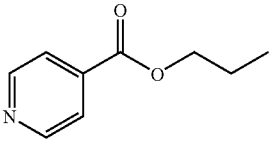 | 9.0* (1.7, 47.9) | 15.4* (7.7, 30.7) |
| Decyl isonicotinate (93145-74-5) | 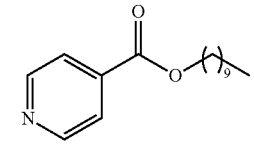 | 14.9 (0.3, 739.5) | 6.8* (1.9, 24.7) |
| Ethyl 4-pyridyl ketone (1701-69-5) | 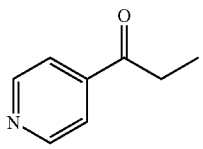 | 19.4* (4.5, 83.9) | 13.5* (7.4, 24.7) |
| Methyl 4-pyridyl ketone (1122-54-9) | 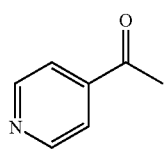 | 0 (0.0, >1000) | 7.6* (2.1, 27.4) |
| Pyridine, 4-(1,3-dioxalan-2-yl) (61379-59-7) | 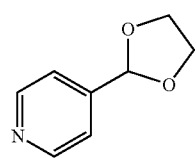 | 16.6 (0.3, 827.2) | 5.3* (1.3, 21.4) |

TABLE 1-continued

Attractant activity of selected compounds of the invention, plus a known
attractant, towards female *Thrips obseuratus* and *Thrips tabaci* in field trials[1]

| Compound (Registry No.) | Structure | Average ratio of female thrips caught relative to water traps (95% CI[2]) | |
|---|---|---|---|
| | | *Thrips obscuratus* | *Thrips tabaci* |
| Ethyl nicotinate (614-18-6) (Known thrips attractant) | [structure] | 157.6* (92.0, 269.9) | 3.1* (1.9, 4.9) |

[1]Ratios of catches of females in baited traps to control traps were analysed using a Poisson generalised linear mixed model with a logit link; * indicates statistically significant difference (P < 0.05) from control trap.
[2]Backtransformed 95% confidence intervals (CI), ± two standard errors.

Example 3

Y-tube Olfactometer

The olfactory behaviour of thrips toward volatile compounds was evaluated in a glass Y-tube olfactometer following the method described by de Kogel et al. (de Kogel, W. J., Koschier, E. H. and Visser, J. H. *Proc. Exper. & Appl. Entomol.*, N. E. V. Amsterdam, (1999) 10, 131-135.) and Koschler et al. (Koschier, E. H., De Kogel, W. J. and Visser, J. H. (2000) *Journal of Chemical Ecology*, 26, 2643-2655.). The Y-tube has two branching arms at an angle of 45° leading into a single tube, all 60 mm long, with an internal diameter of 5 mm. The arms of the Y-tube were connected to glass Wheaton Micro Kit® adapters that were in turn attached to 4 ml glass vials each containing a 1 cm² piece of filter paper (Whatman No. 1). The Y-tube and Wheaton apparatus were placed in a grey-box (to prevent external stimuli influencing thrips' behaviour), located in a darkened, air-conditioned room (22±3° C.). The Y-tube was placed at an inclining position of 25° between the Y-tube and horizontal plane and illuminated from above by a halogen lamp (780 lux). One microliter of the volatile compounds, either undiluted or diluted in hexane (95%, Pronalys AR), was applied to filter paper in one vial, while 1 μl of hexane was applied to filter paper held in the second vial. Air was drawn through activated charcoal before entering the Wheaton apparatus and Y-tube using a suction pump (AR Harris Co. Ltd, Christchurch) producing an airflow of 5 cm/s through each arm and 10 cm/s at the base of the Y-tube. Air was drawn through for 30 min before introducing the first thrips. Connections between the activated charcoal, Wheaton apparatus, Y-tube and suction pump consisted of silicone tubing.

An individual female *Frankliniella occidentalis* thrips of unknown age, that had been starved overnight, was released into the Y-tube using a small aspirator. The aspirator was made by placing a 1 ml pipette tip over the end of silicone tubing (5 mm diameter) the end of which was covered with fine mesh; the pipette tip was cut so it projected 5 mm beyond the end of the silicone tubing. A thrips was sucked up into the pipette tip, which was then placed at the base of the Y-tube. Most thrips walked up into the Y-tube within a few seconds, at which time the silicone air suction tubing was reconnected to the glass Y. The choice between clean or odour laden airflow was recorded when the thrips reached the far end of one arm and only those thrips that made the choice within 3 min were recorded. After every 5 thrips the Y-tube and Wheaton apparatus were rotated 1800 to avoid position effects. After 25 choices were recorded, the Y-tube and Wheaton apparatus were thoroughly cleaned with acetone (99.5%, BDH) and allowed to dry before repeating the experiment. Each compound and dilution was replicated 3 times.

The results from the Y-tube experiments are shown in Table 2.

TABLE 2

Attractant activity of selected compounds of the invention, plus a known attractant, towards female *Frankliniella occidentalis* in a Y-tube olfactometer

| Compound (Registry No.) | Structure | MAC (%)[1] | % Response (t value)[2] | Comment |
|---|---|---|---|---|
| Methyl isonicotinate (2459-09-8) | [structure] | 0.0001 | 74.7 (<0.001) | — |

TABLE 2-continued

Attractant activity of selected compounds of the invention, plus a known attractant, towards female *Frankliniella occidentalis* in a Y-tube olfactometer

| Compound (Registry No.) | Structure | MAC (%)[1] | % Response (t value)[2] | Comment |
|---|---|---|---|---|
| Ethyl isonicotinate (1570-45-2) | 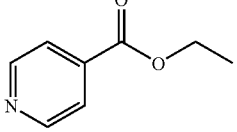 | 0.001 | 60.0 (0.043) | — |
| iso-Propyl isonicotinate (125294-42-0) | 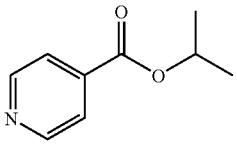 | 1 | 66.7 (0.002) | — |
| n-Propyl isonicotinate (90610-01-8) | 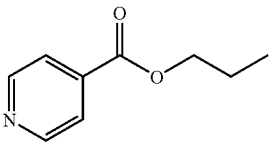 | 0.1 | 61.3 (0.026) | — |
| Ethyl 2-chloro-isonicotinate (54453-93-9) | 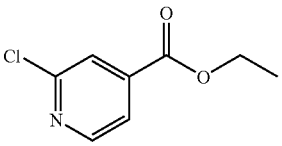 | 0.0001 | 65.3 (0.005) | — |
| Di-iso-Propyl isonicotinate (77924-05-1) | 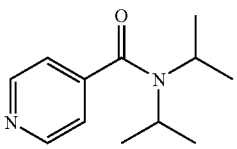 | <100 | 81.3 (<0.001) | — |
| Methyl 4-pyridylketone (1122-54-9) | 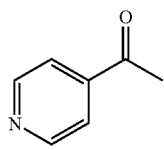 | 0.001 | 77.3 (<0.001) | — |
| Ethyl 4-pyridyl ketone (1701-69-5) | 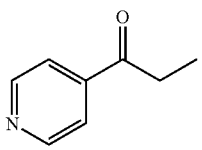 | 1 | 68.0 (0.001) | — |
| n-Propyl 4-pyridyl ketone (1701-71-9) | 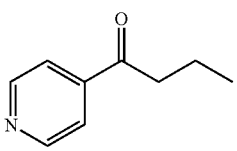 | 100 | 54.7 (0.282) | — |
| Pyridine, 4-(1,3-dioxolan-2-yl) (61379-59-7) | 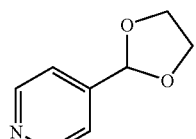 | 1 | 62.7 (0.015) | |

TABLE 2-continued

Attractant activity of selected compounds of the invention, plus a known attractant, towards female *Frankliniella occidentalis* in a Y-tube olfactometer

| Compound (Registry No.) | Structure | MAC (%)[1] | % Response (t value)[2] | Comment |
|---|---|---|---|---|
| 4-Formylpyridine (872-85-5) | 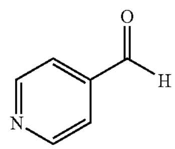 | 0.001 | 66.7 (0.002) | Repellant > 0.01 |
| 4-Cyanopyridine (100-48-1) | 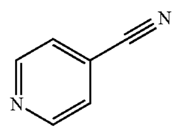 | <100 | 38.7 (0.026) | Repellant |
| 4-Pyridyl thioacetate (36875-66-8) | 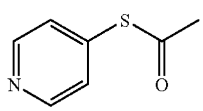 | <100 | 26.7 (<0.001) | Repellant |
| Ethyl nicotinate (614-18-6) (Known thrips attractant) | 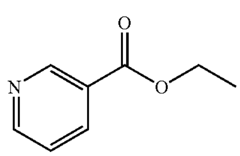 | 0.01 | 60.0 (0.043) | — |

[1]MAC = Minimum Active Concentration (i.e. minimum concentration to elicit a response from thrips (P < 0.05), data was analysed using a binomial generalised linear model with a logit link).
[2]Percentage of thrips to walk up odour-laden arm Example 4

Greenhouse Trials

Greenhouse trials were undertaken using water traps similar to those used in the field trials (Example 2), or yellow sticky traps (Veg-Gro Supplies Ltd, Auckland) to examine the response of thrips to volatile compounds. The greenhouse, located in Auckland, is ≈88×200 m, constructed of glass, and is used to grow capsicum (*Capsicum annuum* var. Special, Fiesta, Boogie and Stirit). Water traps were placed 20 to 24 m apart within a row and 24 m apart between rows. There were 6 baited water traps for each compound tested and 6 water-only traps randomly positioned in a 6×2 grid in the greenhouse. Traps were positioned just above the crop canopy. Water traps (2 L containers, 16×16×8.5 cm) were assembled as described in Example 2 and left in the greenhouse for 24 h, after which time the containers were sealed for transport to a laboratory. Insects from each water trap were transferred to 5 ml glass tubes containing 75% ethanol within 24 h of collecting them from the greenhouse. Catches from each treatment were analysed under a stereomicroscope (100×) and the proportion of *Frankliniella occidentalis* was determined.

Yellow sticky traps (24.4×20 cm) were treated with a compound or water using a 30 ml spray mist dripulator (Arthur Holmes, Wellington) held 10 cm away from the sticky trap. Four sprays were applied to each side, coating the sticky trap in approximately 1 ml of water or compound. Sticky traps sprayed with the same treatment were separated using black metal foldback clips (19 mm, Celco), suspended within a cardboard box (29.5×22.3×30.2 cm), which was in turn sealed within a plastic bag for transport to the greenhouse. Traps were suspended in the greenhouse just above the crop canopy within 3 h after spraying, using the same layout as for the water traps (20 to 24 m apart within a row, 24 m between rows, in a 6×2 grid). After 24 h the traps were collected by wrapping each trap in plastic wrap for transport to the laboratory. The total number of thrips on the traps were counted using 10× magnification. Thrips were removed from the sticky traps using De-Solv-it® and Johnsons baby oil®. A subsample from each treatment was further analysed under a stereomicroscope (100×) and the proportion of *Frankliniella occidentalis* was determined.

TABLE 3

Attractant activity of selected compounds of the invention, plus a known attractant, towards thrips in greenhouse trials (>95% of thrips caught on sticky traps and around 66% of thrips caught in water traps were *Frankliniella occidentalis*).

| Compound (Registry No.) | Structure | Trap type | Average ratio of thrips caught relative to water treated traps (t-value)[1] |
|---|---|---|---|
| Methyl isonicotinate (2459-09-8) | 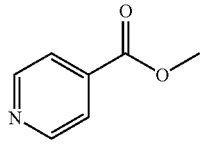 | Water trap | 4.3 (5.7) |
| Methyl isonicotinate (2459-09-8) | 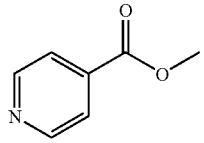 | Yellow sticky trap | 3.7 (8.1) |
| Ethyl isonicotinate (1570-45-2) | 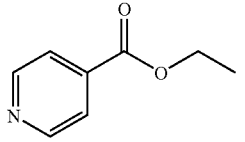 | Water trap | 2.2 (2.8) |
| Ethyl isonicotinate (1570-45-2) | 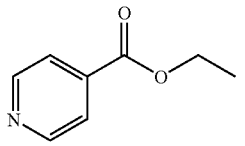 | Yellow sticky trap | 2.6 (3.9) |
| Ethyl 2-chloro-isonicotinate (54453-93-9) | 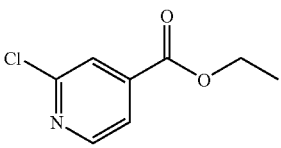 | Yellow sticky trap | 1.8 (2.8) |
| Methyl 4-pyridylketone (1122-54-9) | 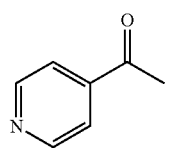 | Yellow sticky trap | 3.1 (6.6) |
| Ethyl nicotinate (614-18-6) | 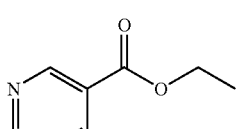 | Water trap | 1 (0.1) |
| Ethyl nicotinate (614-18-6) (Known thrips attractant) | 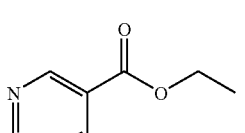 | Yellow sticky trap | 1.1 (0.4) |

[1] Ratios were analysed using a Poisson generalised linear mixed model with a logit link. All compounds except ethyl nicotinate, caught significantly more thrips ($P < 0.001$) than the water-only traps.

Although the invention has been described by way of example, it should be appreciated that variations and modifications may be made without departing from the scope of the invention. Furthermore, where known equivalents exist to specific features, such equivalents are incorporated as if specifically referred to in this specification.

The invention claimed is:

1. A method of controlling or surveying thrips populations comprising providing at least one thrips behaviour-modifying compound selected from the group consisting of:
   methyl isonicotinate;
   propyl Isonicotinate;
   isopropyl isonicotinate;
   decyl isonicotinate;
   ethyl 2-chloro-isonicotinate;
   pyridine, 4-(1,3-dioxolan-2-yl);
   di-isopropyl isonicotinamide;
   4-formyl pyridine;
   methyl 4-pyridyl ketone;
   ethyl 4-pyridyl ketone;
   propyl 4-pyridyl ketone;
   4-cyanopyridine; and
   4-pyridyl thioacetate;
   and immobilizing, catching, removing or killing thrips, or estimating or monitoring thrips populations.

2. The method according to claim 1 wherein the at least one thrips behaviour-modifying compound is provided in a holding device wherein the at least one compound attracts thrips to the holding device.

3. The method according to claim 2 wherein the holding device includes a means for immobilising or killing thrips.

4. The method according to claim 2 wherein the holding device is selected from the group comprising a water trap, a sticky trap and a pheromone trap.

5. The method according to claim 1 wherein the at least one behavior-modifying compound is provided by applying it to plants selected from the group consisting of onions, lettuce, cabbage and other crucifers, greenhouse vegetables, greenhouse fruits, and flower crops.

6. A method of preventing or minimising damage to plants caused by thrips, comprising repelling thrips away from the plants by providing at least one thrips-repelling compound selected from the group consisting of:
   4-formyl pyridine;
   4-cyanopyridine; and
   4-pyridyl thioacetate.

7. The method of claim 1 wherein at least one of a behaviour-modifying compound that is a thrips attracting compound and at least one of a behaviour-modifying compound that is thrips-repelling are provided and wherein the thrips-attracting compound is selected from the group consisting of:
   methyl isonicotinate, propyl isonicotinate, isopropyl isonicotinate, decyl isonicotinate, ethyl 2-chloro-isonicotinate, pyridine, 4-(1,3-dioxolan-2-yl), di-isopropyl isonicotinamide, 4-formyl pyridine, methyl 4-pyridyl ketone, ethyl 4-pyridyl ketone and propyl 4-pyridyl ketone
and the thrips-repelling compound is selected from the group consisting of:
   4-formyl pyridine, 4-cyanopyridine and 4-pyridyl thioacetate.

8. The method of claim 1 comprising additionally providing at least one other thrips attractant or thrips repellant.

9. The method according to claim 8 wherein the at least one other thrips attractant or thrips repellant is selected from the group consisting of:
   ethyl nicotinate, anisaldehyde, cinnamaldehyde, methyl anthranilate, ethyl anthranilate, decyl acetate, dodecyl acetate, eugenol, beta-ionone, o-methoxy cinnamic aldehyde, methyl salicylate, ethyl salicylate, monoterpene 1,8-cineole, salicaldehyde, o-aminoacetophenone, isobornyl valerate, methyl benzoate, ethyl benzoate, 2-phenyl ethanol and p-allyl anisole.

10. The method according to claim wherein the thrips populations are those belonging to the sub-order Terebrantia.

11. The method according to claim wherein the thrips populations are *Thrips obscuratus*, *Thrips tabaci* or *Frankliniella occidentalis*.

12. The method according to claim 11 wherein the thrips population is *Frankliniella occidentalis*.

13. The method according to claim 1, wherein the compound is methyl isonicotinate.

14. The method according to claim wherein the thrips population is *Frankliniella occidentalis*.

* * * * *